United States Patent [19]

Astrahan et al.

[11] Patent Number: 5,220,927
[45] Date of Patent: Jun. 22, 1993

[54] URETHRAL INSERTED APPLICATOR FOR PROSTATE HYPERTHERMIA

[75] Inventors: Melvin A. Astrahan, Los Alamitos, Calif.; Paul F. Turner, North Salt Lake, Utah

[73] Assignee: BSD Medical Corporation, Salt Lake City, Utah

[21] Appl. No.: 495,736

[22] Filed: Mar. 15, 1990

Related U.S. Application Data

[63] Continuation-in-part of Ser. No. 225,307, Jul. 28, 1988, Pat. No. 4,967,765.

[51] Int. Cl.$^5$ .............................................. A61N 5/02
[52] U.S. Cl. .................................. 128/785; 128/786; 128/804; 128/736
[58] Field of Search ........................... 128/804, 784–786, 128/788, 736, 401

[56] References Cited

U.S. PATENT DOCUMENTS

| | | | |
|---|---|---|---|
| 4,154,246 | 5/1979 | LeVeen | 128/784 |
| 4,311,154 | 1/1982 | Sterzer et al. | 128/804 |
| 4,448,198 | 5/1984 | Turner | 128/422 |
| 4,524,550 | 7/1985 | Ruggera et al. | 128/1.5 |
| 4,583,556 | 4/1986 | Hines et al. | 128/804 |
| 4,601,296 | 7/1986 | Yerushalmi et al. | 128/804 |
| 4,658,836 | 4/1987 | Turner | 128/804 |
| 4,669,475 | 6/1987 | Turner | 128/399 |
| 4,676,258 | 6/1987 | Inokochi et al. | 128/804 |
| 4,681,122 | 7/1987 | Winters et al. | 128/736 |
| 4,700,716 | 10/1987 | Kasevich et al. | 128/804 |
| 4,712,559 | 12/1987 | Turner | 128/422 |
| 4,813,429 | 3/1989 | Eshel et al. | 128/736 |
| 4,860,752 | 8/1989 | Turner | 128/422 |
| 4,967,765 | 11/1990 | Turner et al. | 128/804 X |
| 5,007,431 | 4/1991 | Sterzer | 128/804 |

FOREIGN PATENT DOCUMENTS

| | | | |
|---|---|---|---|
| 3534124 | 4/1987 | Fed. Rep. of Germany | 128/788 |
| 8103616 | 12/1981 | PCT Int'l Appl. | 128/804 |

OTHER PUBLICATIONS

*Medical Tribune*, vol. 29, No. 9, Thursday, Mar. 31, 1988, "Transurethral Hyperthemia for BPH: Trial's Goal is to Top 80% Success," by Rick McClure, pp. 3, 13, 14.

Astrahen et al, "Microwave Applicator . . . Hyperplasic", Int. J. Hyperthemia, 1989, vol. 5, No. 3, 283–286.

Andrew Wu, et al., "Performance Characteristics of a Helical Microwave Interstitial Antenna for Local Hyperthermia", Mar./Apr. '87, Med. Phys, 14(2), pp. 235–237.

El-Deek M. El-Sayed et al., "Use of Sheath Helix Slow-Wave Structure as an Applicator in Microwave Heating Systems" 1981, Journal of Microwave Power, 16 (3&4), pp. 283–288.

(List continued on next page.)

*Primary Examiner*—Lee S. Cohen
*Attorney, Agent, or Firm*—Mallinckrodt & Mallinckrodt

[57] ABSTRACT

A urethral inserted applicator for prostate electromagnetic hyperthermia includes apparatus for holding and positioning at least one electromagnetic energy applicator in a urethral passage extending through a prostate gland. The apparatus includes a multi-passage or multi-tube, balloon type urinary or Foley catheter with fluid-dry passages for insertion of microwave antenna or capacitive electrode type applicators, and an electromagnetic compatible type temperature sensor for measuring the temperature of the prostate tissue. The urinary catheter provides an open fluid receiving tube enabling urine drainage from the bladder and a balloon at the tip region of the catheter for engaging the bladder neck to properly position and hold the apparatus during treatment. An electromagnetic generator supplies electromagnetic energy to the applicators. A comparator is connected to the temperature sensor and a temperature reference potentiometer for comparing the actual tissue temperature with a desired temperature and for providing output control signals to the electromagnetic generator for controlling the output of the generator to the applicators. The insertable coaxial applicators can be any type constructed with small coaxial cable.

24 Claims, 9 Drawing Sheets

OTHER PUBLICATIONS

Jozef Mendecki et al., "Microwave Applicators for Localized Hyperthemia Treatment of Cancer of the Prostate", Nov. '80, Int. J. Radiation Biol. Phys., V. 6, No. 11, pp. 1583–1588.

Tadashi Harada, et al., "Microwave Surgical Treatment of Diseases of Prostate", Urology, Dec. '85 vol. XXVI No. 6, pp. 572–576.

Ding-Jiu Li, et al. "Design & Thermometry of an Intracavitary Microwave Applicator Suitable for Treatment of Some Vaginal & Rectal Cancers", Nov. '84 Int. J. RadiationOncology Biol. Phys. V. 10, pp. 2155–2162.

Leonid Leybovich, et al., "Intracavitary Hyperthermia: A Newly Designed Applicator for Tracheal Tumors:", Jan. '87, Endocurietherapy/Hyperthermia Oncology, V. 3, pp. 23–29.

Toru Satoh, et al., "Thermal Distribution Studies of Helical Coil Microwave Antennas for Interstitial Hyperthermia", Int. J. Radiation Oncology Biol. Phys. vol. 15, pp. 1209–1218.

P. B. Dunscombe et al., "Heat Production in Microwave-Irradiated Thermocouples", Med. Phys. 13 (4), Jul./Aug. 1986.

R. T. Constable et al., "Perturbation of the Temperature Distribution in Micro-wave Irradiated Tissue Due to the Presence of Metallic Thermometers", Med. Phys. 14 (3), May/Jun. 1987.

Transactions on Biomedical Eng. Leonard S. Taylor, "Electromagnetic Syringe", vol. BME-25, No. 3, May 1978.

*Medical Tribune*, vol. 29, No. 9, Thursday, Mar. 31, 1988, "Transurethral Hyperthermia for BPH: Trial's Goal is to Top 80% Success," by Rick McClure, pp. 3, 13, 14.

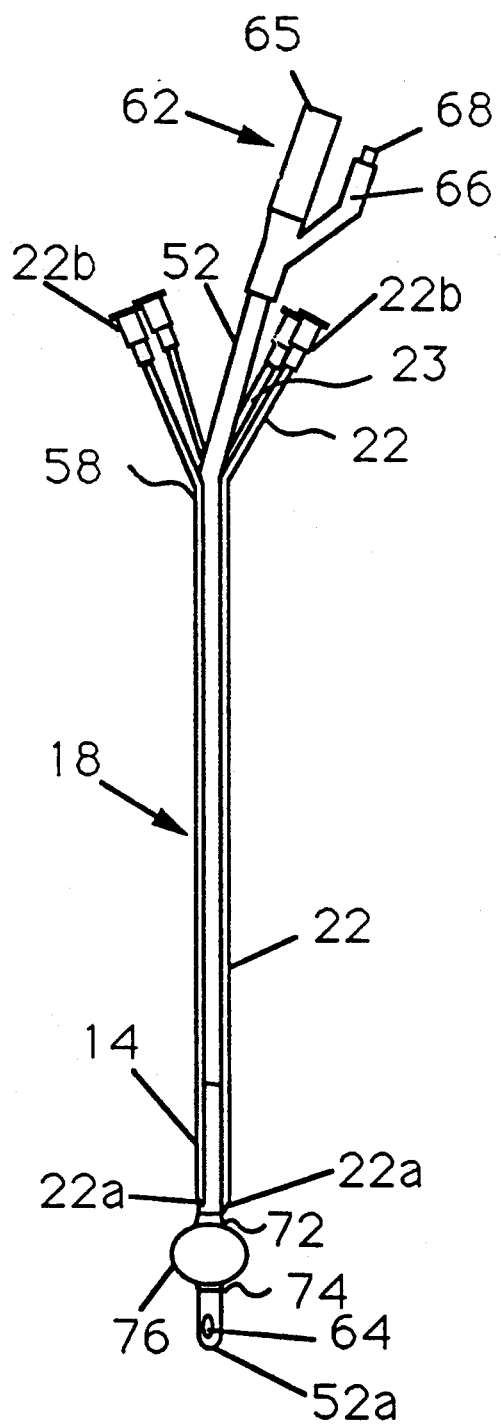
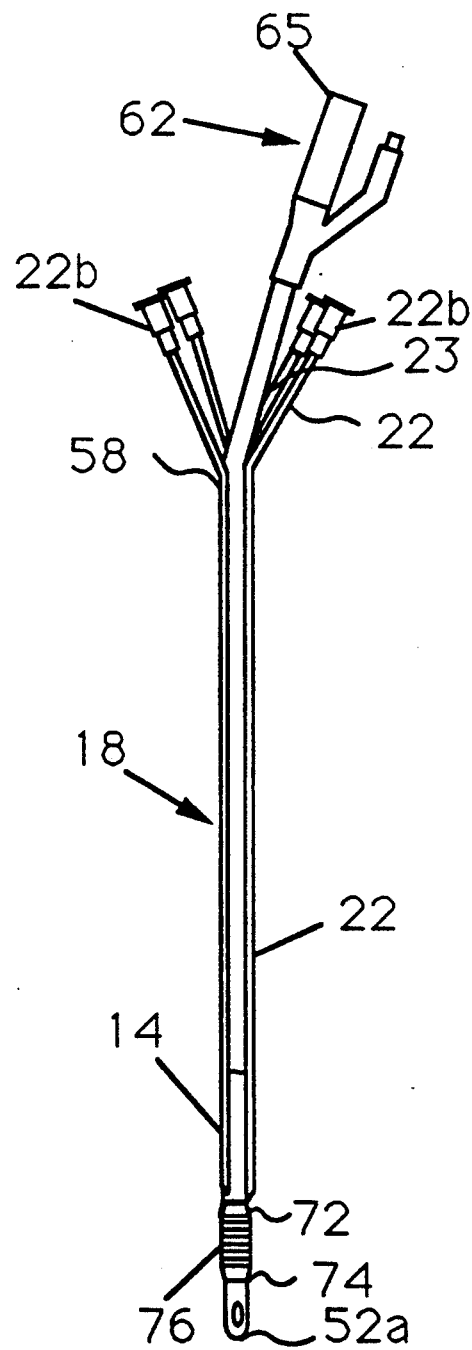
FIGURE 3
FIGURE 4

URETHRAL INSERTED APPLICATOR FOR PROSTATE HYPERTHERMIA

RELATED APPLICATIONS

This is a continuation-in-part of copending application Ser. No. 07/255,307, filed Jul. 28, 1988, now U.S. Pat. No. 4,967,765, entitled Urethral Inserted Applicator for Prostate Hyperthermia, Paul F. Turner, Inventor.

BACKGROUND OF THE INVENTION

1. Field

This invention relates to electromagnetic radiation antenna or electrode devices for medical hyperthermic purposes, and more particularly to a combined catheter and electromagnetic or microwave applicator for treating prostatomegaly such as benign prostatic hypertrophy, prostatitis, and prostate malignancy by urethral insertion.

2. State of the Art

Hyperthermia or induced high body temperature has been considered beneficial in treating various human diseases including many types of cancer. More specifically, various types of malignant growths are considered by many researchers to have a relatively narrow hyperthermia treatment temperature range. Below a threshold temperature of about 41.5 degrees Celsius, thermal destruction of these malignancies is not possible, and, in fact, their growth may be stimulated. However, at temperatures above a range of about 43 to 45 degrees Celsius thermal damage to most normal body tissue cells occurs if exposure lasts for even a relatively short duration.

While some types of skin cancers are known to respond to direct application of surface heat, deeply located malignant growths, owing to normal blood flow body heat transfer properties of the body, were most difficult to heat to the desired temperature without damaging overlying healthy tissue. A solution to this problem has been the development of electromagnetic radiation (EMR) heating devices for inducing hyperthermia. This form of treatment is known as "diathermia".

EMR heating of subsurface growths from an exterior surface is ordinarily enabled by configuration and placement of one or more applicators and by appropriate selection of EMR frequency, phase, and intensity. Nevertheless, tissue growths inside of, or in close proximity to, heat sensitive tissue or organs, are much more effectively and safely heated by EMR irradiating applicators positioned within the body as closely as possible to the growth requiring treatment.

The advantages of positioning EMR applicators relatively close to the growth to be heated by radiation include improved heating control, more localized heating and consequently less possibility of overheating adjacent healthy tissue and more direct treatment of the enlarged tissues causing the undesirable symptoms.

Close applicator access to certain types of diseased tissue growths is provided by surgical procedures for naturally occurring body passages such as the esophagus, larynx, prostate gland and colon. Surgical procedures enlarge the passage by cutting away the passage tissue. Some heating methods use small EMR applicators placed over the tissue or in an incision to provide direct irradiation of the growth. An illustrative type of body passage insertable EMR applicator is described in U.S. Pat. No. 2,407,690 issued to Southworth. The Southworth type body passage EMR applicators have been configured to cause a heating pattern that tends to be concentrated at the radiating tip of the applicator and which decreases at a usually exponential rate from such tip towards the radiation source.

Special and difficult problems often attend growths found along natural body passages. For example, diseased tissue tends to spread around and along the passage, often in a relatively thin layer. Typically, the diseased layer may be less than a centimeter thick and may extend as far as 6–10 centimeters along the passage. The use of Southworth type applicators result in nonuniform irradiation heating of the elongated growth. Thus, the temperature at the tip of the Southworth type applicator may have to be so hot that it kills surrounding healthy tissue in order to make the portion of the applicator toward the radiation source, i.e. power supply, hot enough to kill the growth.

Ridged and non-flexible antenna rectal inserted devices are known. Examples of such devices are disclosed in U.S. Pat. No. 4,601,296 issued to Yerushalmi, and a 1980 article titled "Microwave Applicators for Localized Hyperthermia Treatment of Cancer of the Prostate" by Mendecki et al., Int. J. Radiation Oncology, Biol. Phys., Vol. 6, pp. 1583 and 1588.

Also, helical coil designs have been used to heat tissues placed within the cylindrical opening of the device. Such devices are disclosed in U.S. Pat. No. 4,527,550 issued July 1985 to Ruggera.

A body passage insertable applicator apparatus for EMR systems is known that includes a urethral inserted probe having a monopole antenna (Microwave Surgical Treatment of Diseases of Prostate, Harada et al., Urology, December 1985, Vol. XXVI, No. 6, pp. 572–576). This device of Harada has no position fixing device to reliably provide correct placement. It also does not include a temperature monitoring device to monitor the prostate tissue or a means of controlling the treated prostate tissue at a preset target temperature. The Harada device does not include a fluid drainage device to enable urine drainage for prolonged treatment. The Harada device is described as more of a microwave surgery device which applies a large amount of power to a short length of tissues for a short time to cause lethal damage to the tissues. If a longer length of tissues along the urethra is to be treated, multiple treatment of short, adjacent lengths of tissue are required with the antenna manually repositioned along the urethra between each treatment. Tissue temperatures far above 50 degrees Celsius are intended in treated tissues to cause tissue coagulation of the treated tissues. This high controlled temperature is noted by Harada to have caused "destruction of the prostate itself" in animal experiments. "On histologic examination, an extensive necrotic region with hemorrhage was noted immediately after the procedure". Although the Harada device and procedure appeared to provided some benefit to some patients, the uncontrolled procedure and system presents undesirable possible risk to the patients. The difficulty in positioning, controlling, and the general use of the Harada devices appears not very practical since the suggested normal positioning is by "rectal examination or transabdonimal echography."

Also known is a helical wound coil applicator having coaxial inner and outer conductors electrically connected at an EMR input end to a conventional coaxial transmission line for transmitting high frequency EMR from a source to the applicator. The applicator outer conductor is longitudinally split on opposite sides to form first and second outer conductor segments. The inner conductor is electrically connected to an applicator termination end of one of such segments. A dielectric media is disposed between the applicator inner and outer conductors, and the outer conductor and termination end are covered by a dielectric sheath. A substantially uniform, external electric tissue heating field is obtained along substantially the entire length of the applicator by exponentially increasing the thickness of the dielectric sheath over the termination end equal to at least half the outer diameter of the applicator. Those persons skilled in the art desiring further information concerning this device are referred to U.S. Pat. No. 4,658,836 issued Apr. 21, 1987 to Paul F. Turner. This helical coil style antenna design was described by Andrew Wu, M. L. Watson, E. S. Sternick, R. J. Bielawa and K. L. Carr as a suitable microwave interstitial antenna type in Med. Phys. 14(2), Mar/Apr 1987, page 235-237. Satoh, Stauffer, and Fike described use of a helical coil antenna as a microwave interstitial applicator in the Int. J. of Radiation Oncology Biology, and Physics, Vol. 15, Nov. 1988, pgs. 1209-1218. Microwave Interstitial coaxial type applicators were also described by L. Taylor in IEEE Trans. on Biomedical Engineering, BME-25, No. 3, May 1978, pg. 303.

SUMMARY OF THE INVENTION

A principal feature distinguishing the present invention from prior art devices is the provision of a urethral insertable EMR applicator principally adapted for benign prostatic hyperplasia (BPH), which provides the generally cylindrical and longitudinally uniform EMR heating pattern necessary to enable substantially uniform heating of BPH growths or other tissue diseases associated with the urinary track.

Accordingly, it is an object of the invention to provide an improved or alternate treatment to surgery for the symptomatic relief of prostatomegaly which primarily results in blockage of the prostatic urethra. This disease condition includes prostatitis, benign prostatic hyperplasia and prostatic malignancy as well as other diseases of the prostate gland locally involved around the urethra.

Another object of the invention is to provide an EMR applicator apparatus meeting the clinical requirements of high flexibility, sterilization, disposability, low cost, urinary drainage, and which can also provide for integral temperature monitoring along the perimeter of the urethral wall.

Yet another object of the invention is to provide an urethral insertable EMR applicator and Foley catheter system which provides the generally cylindrical or longitudinally uniform EMR heating pattern necessary to enable approximately uniform heating of the prostate tissues or other diseased tissues associated with the urinary track.

A further object of the invention is to provide an urethral insertable EMR applicator or applicators which can be positioned with respect to the prostate and maintained against movement therefrom during treatment.

Briefly stated, the urethral EMR applicator system includes a controlled source of EMR connected to one or more coaxial antenna applicators or electrodes which are inserted into receiving passages of a Foley style urinary drainage catheter. The receiving passages may be plastic or rubber tubes which have been attached to the outer wall of the catheter, may be such tubes embedded in the wall of the catheter, or may be receiving passages formed integrally with the wall of the catheter. A temperature controller includes a sensor for determining the temperature of the surrounding tissue and generating control signals for the source of EMR.

The system includes an applicator holding and positioning apparatus for automatically positioning the inserted applicators adjacent the prostate gland and for maintaining the position during the treatment. The inserted coaxial electrode or antenna applicator (or applicators) are suitably sheathed to provide an external substantially uniform electromagnetic heating field to be radiated at nearly all transverse cross sections along the applicator for approximately uniform tissue heating.

The applicator holding and positioning apparatus includes a flexible urinary catheter, such as a Foley catheter, having substantially tubular shaped and an insertion end for insertion through the urethral passage and bladder neck to the bladder. This type of catheter provides a fluid drainage means to remove fluid filling the bladder and also includes balloon means mounted on the urinary catheter near the insertion end and adapted to be inserted into the bladder with the insertion end of the catheter. Means are provided for inflating the balloon when it is in the bladder so that the inflated balloon will seat in the bladder neck to thereby hold the inserted urinary catheter in fixed position in the urethral passage, regardless of changes in length of such passage during treatment. One or more applicator receiving passages are provided in the apparatus sized to receive electromagnetic energy applicators therein. The receiving passages may be tubes secured, such as by a silicone rubber adhesive, to the perimeter of the urinary catheter, tubes embedded in the wall of the urinary catheter, or passages formed integrally with the catheter. The applicator receiving passages extend along the urinary catheter toward the insertion end of the catheter a distance sufficient so that with the urinary catheter in place in the urethral passage, the applicator receiving passages extend substantially through the prostate gland so that the EMR applicators placed in the receiving passages are within the prostate and can apply EMR energy to the prostate tissue surrounding the urethral passage to thereby heat such tissue. There are preferably two or three applicator receiving passages spaced uniformly around the urinary catheter. It is also preferred to provide a temperature sensor receiving passage similar to the applicator receiving passages for receiving a temperature sensor to be positioned in the prostate to measure the temperature of the prostate tissue during treatment. However, temperature sensors can be positioned along with the applicators in the applicator receiving passages so the temperature sensor receiving passage is not always necessary.

The inserted applicator or applicators may either be comprised of radiating coaxial type antennae or they may be comprised of capacitively isolated electrodes which operate below the 300 MHz microwave band. The electrode applicator system at lower frequencies (typically 100 kHz to 300 MHz) may utilize applicators which apply energy of differing phases so currents flow between the applicators or may utilize a secondary electrode either placed on the patients skin surface, into the rectal region, or simply connected to a large conductive ground plane such as a metal table top of the earth ground surface. This secondary electrode provides a current flow return path for the currents directed into the tissue by the lower frequency electrodes.

The present invention provides a low cost, disposable EMR applicator holding and positioning apparatus which allows EMR applicators to be detachably placed therein and which keeps such applicators securely in position in a prostate gland during treatment, the apparatus can also provide for holding and positioning of temperature sensors.

BPH is usually treated by surgery with significant side effects. These side effects include hermorrhage, impotency, anesthetic complications, and technical failures. The use of the present invention involves a treatment which requires no anesthesia or surgery and requires only 1 or 2 hour office visits to accomplish in comparison to post surgical hospitalization.

THE DRAWINGS

Other objects and features of the invention will become more readily apparent from the following detailed description when read in conjunction with the accompanying drawings, in which:

FIG. 3 is an elevational view showing the modified Foley catheter insertion apparatus of the invention with the balloon section inflated;

FIG. 4 is an elevational view showing the modified Foley catheter insertion apparatus of the invention with the balloon deflated;

DETAILED DESCRIPTION OF A PREFERRED EMBODIMENT

Figure 1:
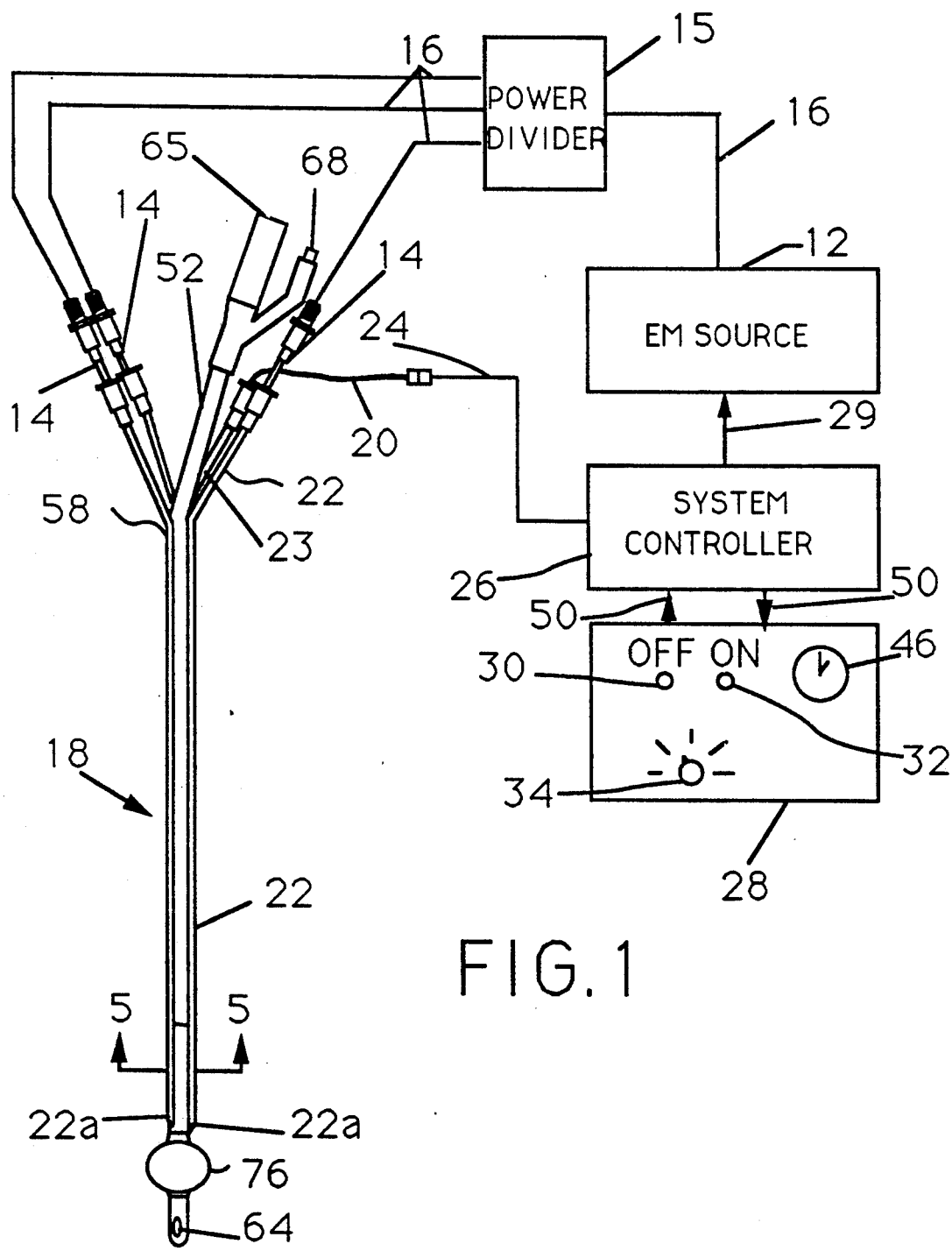
FIG. 1 is an elevational view of the urethral insertable EMR microwave applicator system with a portion of the system shown schematically in block form.

Referring now to FIG. 1, the illustrated urethral insertable electromagnetic radiation (EMR) applicator system includes an electromagnetic energy (EM) source 12 for supplying electromagnetic energy to electromagnetic heating applicators 14 through a power divider or multi-channel amplifier 15 and connecting cables 16. If only a single applicator 14 is used, there is no need for item 15 and the coaxial cable 16 connects directly from generator 12 to applicator 14.

Electromagnetic energy source 12 includes an oscillator for supplying a maximum of about 40 watts electrical power at a frequency of between 300 to 2450 MHz if applicators 14 are microwave radiating antenna type applicators, or at a frequency of between 100 kHz to 300 MHz if applicators 14 are electrode type applicators. Power divider 15 preferably provides equal phase for each of the outputs when microwave operational frequencies are used. Cables 16 are preferably coaxial cables typically 0.8 to 1.2 mm diameter with 50 ohms impedance. However, the transmission line sections of applicators 14 and cable 16 may be other common types of transmission lines such as two twisted wires. The transmission lines within the antenna 14 could also be a single wire connected to the tip electrode or radiating section of the antenna 14, but the coaxial cable is normally considered the preferred configuration.

Each applicator 14 is an emitter of electromagnetic energy from a partially flexible metallic surface such as a small diameter metal tube, a metal wire braid, a flexible conductive rubber sleeve, a wire coil, several wires coiled, several wire strips, or several metal sleeves inserted or mounted along the perimeter of the applicator holding and positioning apparatus 18 of the invention, which includes a Foley balloon type urinary catheter 52. The catheter 52 is, for example, a size 12 or 14 french catheter modified as hereinafter described. For use at microwave frequencies, the applicator's active heating antenna or antennas could be of many designs all of which are commonly used for Microwave interstitial treatments by insertion into catheters placed into the tissue to be heated. The coaxial antenna or electrode design itself has been previously disclosed in the prior art and is not considered a novel part of this invention.

For frequencies below microwave frequencies, the applicator's active heating zone is referred to as an electrode since the EMR energy is created only in the form of capacitive or nontraveling EMR fields. Thus, in this form, more than one electrode is needed to permit current to flow into the tissue between the electrodes. In the below microwave frequency condition, and with the preferred three applicator or electrode system shown in FIG. 1, the power dividing element 15 produces a three phase output signal with each phase connected to one of the applicators. The three phase signal may be produced by element 15 by internal phase transformers or other phase delay devices such as cable delays, inductor delays, or amplifier delays. These various devices and methods to delay or alter phase for below microwave frequencies are well known to those skilled in the art of electronics. With a three phase output from divider 15, the signal on each applicator or electrode differs in phase by 120 degrees. In this way there is always an electric field potential difference between each of the three inserted electrodes 14 which causes currents to flow in the tissue between these electrodes. The formula from which to determine the preferred phase difference between these electrodes for operation below the microwave frequency range is simply dividing 360 degrees by the number of inserted applicators around the urinary catheter body. For a two electrode system only a two phase output would be needed from power divider 15.

The applicators 14 represent either the microwave antenna type applicator or the lower frequency electrode type applicator and each may be of various designs and may contain one or more of the following physical features:

a) open or closed connection to the tip of the outer conductor metal cylinders or wire coil and center coaxial conductor;

b) open or closed connection to the base of the antenna or electrode inner conductor and the outer coaxial conductor with metal sleeves, braids, or a wire coil;

c) conductor breaks or gaps within the antenna or electrode metal cylinder or coil winding;

d) multiple antenna or electrode gaps in the outer conductor or multiple antenna or electrode coils stacked longitudinally and connected to individual transmission lines, wires or coaxial cable to allow modification of the heat pattern length using either coherent or non-coherent phase energy into each coil;

e) straight but flexible antenna or electrode conductors along the antenna or electrode radiating region to serve as the EM emitters;

f) a coil or electrode sleeve antenna with progressively increasing conductor width or diameter towards the tip of the applicator;

g) an antenna or electrode with center conductor diameter exposed beyond the outer conductor at the tip region;

h) an antenna or electrode which has the center conductor exposed beyond the outer conductor and having an increased metal surface area per unit length closer to the tip region to increase the heating toward the tip region;

i) a wire coil antenna or electrode with different turns ratio per unit length;

j) diameter variations of the center conductor within the electrode or coil length;

k) modification of the dielectric material or thickness around the center conductor or the electrode or coil antenna; and l) a temperature sensor within the antenna region so as to sense the temperature of the surrounding tissue being heated.

Figure 5:
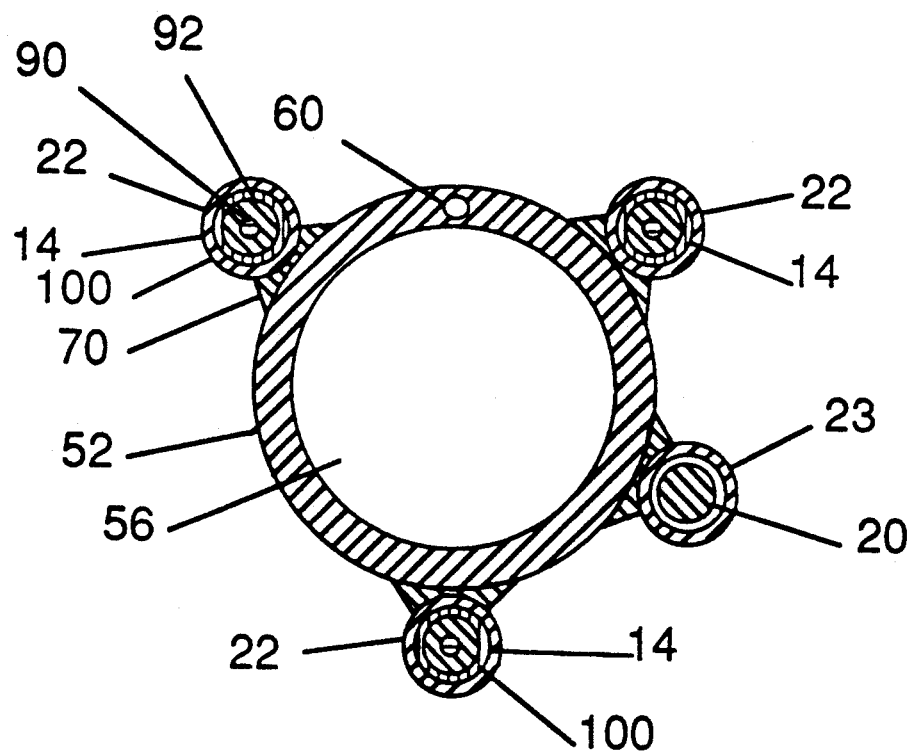
FIG. 5 is a transverse section in the primary heating area of the insertion apparatus taken on the line 5—5 of FIG. 1.

The separable applicators 14 are inserted into applicator receiving passages such as formed by plastic tubes 22 which have been attached, such as by gluing, to the outer wall of the Foley catheter 52. These attached plastic tubes 22 are preferably dry tubes with a sealed inserted tip region 22a, and are uniformly spaced around the circular perimeter surface of the Foley catheter 52, as shown in FIG. 5. This uniform spacing provides for a more uniform heating pattern. Rather than tubes 22 being glued to the outer surface of catheter 52, such tubes could be embedded in the wall of catheter 52, or the applicator receiving passages could be formed integrally with catheter 52.

Figure 2:
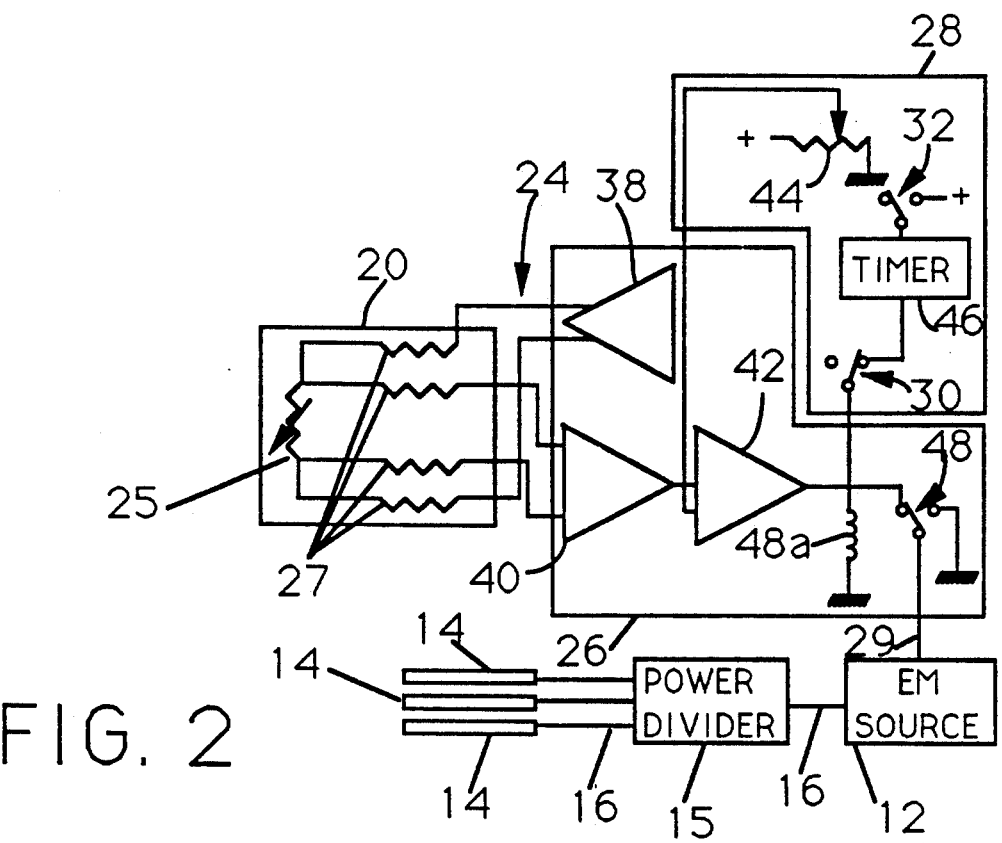
FIG. 2 is a functional schematic view of the temperature sensor and EM energy source control circuits.

A separable insulated temperature sensor 20, shown generally in FIG. 1, and by electrical schematic in FIG. 2, is placed into the region of the device where heating takes place during treatment, preferably by being inserted into a temperature sensor receiving passage such as formed by a flexible plastic tube 23. Tube 23 is attached exteriorly to the Foley catheter 18, such as by gluing, similarly to tubes 22. As with the applicator receiving passages, the temperature sensor receiving passage may alternately be a tube embedded in the catheter or may be formed integrally with the catheter. The temperature sensor measures the temperature of the tissue surrounding the catheter.

The temperature sensor 20 is connected to a system controller circuit 26 by cable 24. The controller circuit controls the operation of the system. This includes controlling the amount of power supplied by the EM source 12 to the EMR applicators 14 in response to the temperature measured by temperature sensor 20 to control and maintain a desired temperature in the tissue being treated. Controller circuit 26 can either be comprised of simple components or can be a micro-processor programmed to provide the temperature and power control function. The output of controller circuit 26 is connected by control cable 29 to the EM energy source 12. Control signals are sent from the controller circuit 26 to the energy source 12 for maintaining the EM power supplied to the applicators sufficient to maintain a tissue temperature between about 41.5 degree Celsius up to 50 degree Celsius. A control and display panel 28 is connected to system controller circuit 26 for two way communication via cable 50. The control and display panel 28 includes EMR energy ON/OFF switch buttons 30 and 32, and a temperature controller knob 34 for setting the desired operating temperature for the temperature sensor circuit and EM or microwave control. These control functions can also be provided by other equivalent forms of displays such as switches, buttons, or computer terminals.

It is important in the system of the invention that the temperature sensor 20 be compatible with the type of heating energy supplied by the system. Thus, normal wire leads in a temperature sensor cannot be used because the electromagnetic energy from the applicators affect the wire leads and causes heating in the leads which results in inaccurate temperature measurement. Resistive leads can be used satisfactorily in an EM field as can optical fiber type temperature sensors. FIG. 2 shows schematically a preferred configuration of temperature sensor 20. The temperature sensor itself is a thermistor 25 provided with insultated resistive leads 27. Two of the resistive leads 27 are connected in parallel to one side of thermistor 25 and the other two resistive leads 27 are connected in parallel to the other side of thermistor 25, as shown. The schematic showing of resistors in leads 27 in FIG. 2 represents the internal resistance of the leads and not separate, additional resistors. Temperature sensor 20 is connected to the controller circuit 26 by four lead cable 24.

The internal components of the controller circuit 26 are shown in FIG. 2 along with the connections to temperature sensor 20. A constant current source 38 is connected through two leads of cable 24 to two of the resistive leads 27 on opposite sides of the thermistor 25. This causes a voltage across the thermistor 25 which changes only as the resistance of the thermistor 25 changes with temperature. This voltage is then directed through the remaining two resistive leads 27 and two leads of cable 24 to a very large input resistance dc amplifier 40. The amplifier input impedance should exceed 100 meg-ohms. Amplifier 40 amplifies the thermister output to a working level. The amplified signal is then passed from the output of amplifier 40 to the input of voltage comparator 42. A reference voltage representative of a desired temperature is set by variable resistor 44 located in control and display panel 28 and controlled by temperature controller knob 34 (FIG. 1), and is sent to a second input of comparator 42. Rather than a variable resistor giving a continuously variable reference voltage, a switchable set of resistors could be used to provide the reference voltage in steps. Voltage comparator 42 compares the temperature related voltage from amplifier 40 with the temperature related reference voltage set by variable resistor 44. The output of comparator 42 provides a signal which is used to control the EMR power supplied from the EM energy source 12 to the applicators 14.

The output signal from comparator 42 is connected through a remotely controlled switch 48, such as a relay, and cable 29 to the EM energy source 12. The switch 48 is controlled by the "on" and "off" switches 32 and 30, respectively, and by timer 46. Upon closing the "on" switch 32, power is supplied to timer 46. Timer 46 supplies power to relay coil 48a to connect the output of comparator 42 to the EM energy source 12. Timer 46 begins a timing cycle when the "on" switch is closed and provides power to relay coil 48a for a preset period of time after closing of the "on" switch. At the end of the preset time, the output of the timer 46 ceases, thereby deenergizing relay coil 48a allowing relay 48 to move to a position to disconnect the output of comparator 48 with EM power source 12 and to ground such connection to turn off the power source. The "off" switch 30 can be used anytime the timer is operating to deenergize relay coil 48a. "Off" switch 30 opens the circuit between timer 46 and relay coil 48a to thereby deenergize the relay and cause EM power generator 12 to stop supplying power.

When connected through switch 48 to EM energy source 12, the output of comparator 42 can be used as a varying voltage control signal for EM power source 12 to vary the output of the power source to applicator 14 in a manner proportional to the voltage of the control signal, or may be used merely to enable or disable the power source so that it either supplies or does not supply energy to the applicators. In either event, the temperature of the monitored tissue is controlled by the controller circuit by controlling the EM power delivered to the applicators 14.

While the control circuit has been shown and described in terms of functional components, the control of the operation of the system can be performed by a computer or microprocessor programmed to preform various of the functions described.

Preferably, the control circuitry and timer will take the form of a special microprocessor which has been programmed to provide the ideal and correct treatment for the patient by automatically controlling the power levels applied to the applicators to maintain the temperature of the tissue being treated at the set desired temperature. With the functional description of the control circuits given herein, it would be within the skill of the art to program a microprocessor or other computer to perform such functions.

While a single temperature sensor has been shown, additional similar temperature sensors may be provided and inserted in additional temperature sensor receiving passages or tubes secured to the catheter 18 similarly to tube 23, or can be otherwise inserted into tissue to be monitored. Further, in some cases, the applicators 14 may have temperature sensors associated therewith which can be used for control purposes.

Figure 6:
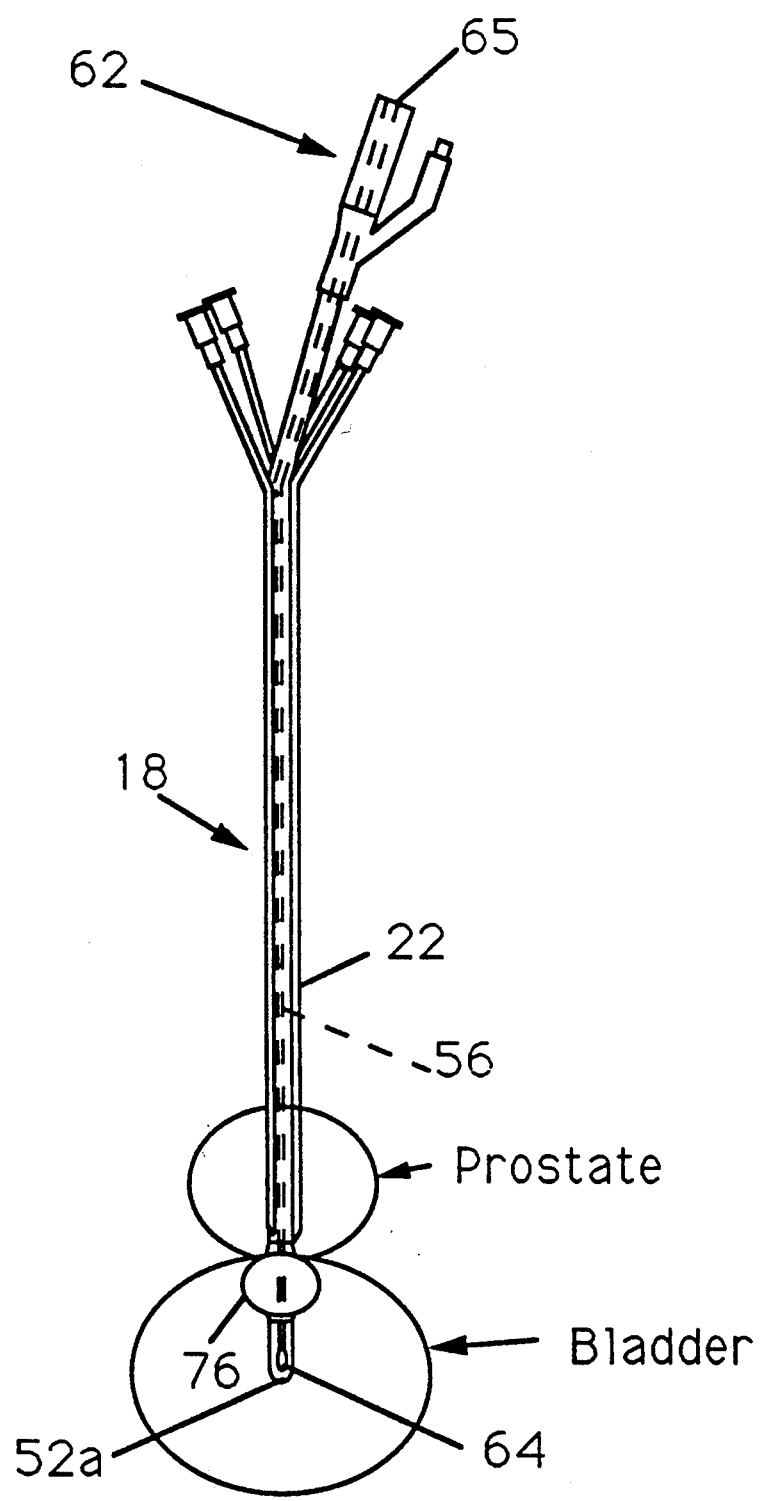
FIG. 6 is a diagrammatic view of the insertion apparatus positioned in the bladder and prostate of a patient showing the treatment positioning of the balloon and Foley catheter to position the applicators in the prostate gland.

FIGS. 3, 4, and 5 show the novel modified urinary or Foley Catheter assembly of the invention which makes it compatible with the separable hyperthermia applicators and temperature sensor. This assembly provides the apparatus for holding and positioning the EMR applicators. As shown, the apparatus, indicated generally at 18, includes an elongate flexible plastic or elastomeric tubular body 52, forming a urinary catheter such as a Foley catheter, with a balloon material 76 secured to balloon stops 72 and 74 near the insertion end 52a of the catheter. A central catheter passage 56, FIGS. 5 and 6, opens through the catheter wall 52 at 64 at the insertion end 52a of the catheter to form a urine drainage tube. At the other end of the catheter, passage 56 opens into a bifurcated "Y" fitting 62 which has an opening at 65 to connect to additional tubing leading to a liquid waste receiving recepticle. The catheter wall 52 also includes a tubular passage 60, FIG. 5, which opens to the outside of the catheter between balloon stops 72 and 74 and beneath the balloon material 76. The other end of passage 60 communicates with "Y" fitting 62 and extends through the fitting arm 66 and is controlled by a valve 68. In use of the device, a pressurized fluid, such as air or water, is forced through passage 60 to inflate balloon 76 as shown in FIGS. 1, 3, and 6. The inflation of the balloon and the retention of the balloon filling fluid is controlled by valve 68. Valve 68 may be a valve which opens when a syringe is inserted therethrough to supply pressurized fluid to inflate the balloon, and which closes to retain pressurized fluid in the balloon when the syringe is removed.

The positioning and holding apparatus 18 includes plastic tubes 22 spaced about the circumference of catheter body 52 to receive the EM applicators therein. Tubes 22 are closed at the insertion tip ends at 22a and terminate at the opposite ends in fittings 22b which accept EM energy applicators 14, as shown in FIG. 1. The tubes 22 are preferably symmetrically spaced about catheter body 52 and are secured thereto by gluing such as with a silicone rubber adhesive 70. Tubes 22 are placed on catheter body 52 with ends 22a accurately and uniformly placed so that applicators 14, when placed in tubes 22, can be accurately positioned a fixed distance from the insertion end 52a of the catheter 52. The applicators 14 are shown positioned in tubes 22 in FIGS. 1 and 5 with FIG. 5 showing the applicator 14 with inner wire conductor 90 surrounded by a cylindrical dielectric material 92, which is in turn surrounded by an outer conductor 100.

In addition to plastic tubes 22 for receiving the applicators 14, a similar plastic tube 23 is secured to catheter body 52 by similar adhesive to accept temperature sensor 20.

In use, the applicator positioning and holding apparatus 18 is inserted through the urethral passage so that it extends in such passage through the prostate and into the bladder. This is shown schematically in FIG. 6. It is thus important that the apparatus 18 be flexible enough to be easily inserted through the urethral passage. When the end of the catheter is in the bladder, pressurized fluid is introduced through valve 68 and fitting 66 into passage 60 to inflate balloon 76 within the bladder. With the balloon inflated in the bladder, the apparatus is pulled outwardly so that the balloon seats in the neck of the bladder. This positively locates and positions the apparatus with respect to the bladder and with respect to the immediately adjacent prostate as shown in FIG. 6. This position of the apparatus remains constant with respect to the bladder and prostate regardless of any variation in length of the urethral passage during treatment.

The EM energy applicators 14 are placed within tubes 22 at a known position, generally at the ends 22a of tubes 22. Since the positions of the applicators 14 in tubes 22 of the apparatus 18 are fixed, and the position of the apparatus 18 is fixed in relation to the prostate, the positions of applicators 14 in the prostate are fixed and remain fixed and constant throughout treatment and the accurate placement of the applicators in the prostate is repeatable from treatment to treatment and from patient to patient. The ability to accurately place the applicators in the prostate without complicated probing, visual imaging, or other positioning procedures, and the stability of the positioning so that the position in the prostate remains constant during treatment, is an important aspect of the invention and important to the practical hyperthermic treatment of the prostate. The placement and positioning of applicators 14 within the tubes 22 may take place prior to or following the insertion of positioning and holding apparatus 18.

During the time the apparatus 18 is in place, central drainage passage 56 of the apparatus serves as a urine drainage tube to allow urine drainage from the bladder. The end 65 of the drainage passage will be connected to tubing leading to a liquid waste receptical.

The coaxial applicators 14 create an external, electromagnetic heating field which extends for a desired length along the applicator from the ends thereof, to create a heating portion of the applicator which extends substantially the length of the tissue in the prostate to be treated. This heating field should be approximately uniform along the length of the heating portion of the applicator. Further direct metallic contact between the metal portions of the applicator and the tissue to be heated should normally be avoided. It may be allowable for such metal surfaces to contact the tissues directly if sufficient protection is provided to assure that potentially dangerous currents at dc or frequencies below 100 kHz cannot flow into the tissues. Such low frequencies can improperly stimulate muscle spasms, cramping, and damage.

In operation, with the apparatus properly positioned as described above, and the timer 46 and the temperature set dial 34 set as desired, the EM generator 12 is turned on by switch 32 and the applicators 14 radiate power into the tissue of the prostate gland extending along the heating portions of the applicator until the desired temperature is reached. When the desired tissue temperature, as set by control 34, is reached, the comparator 42 outputs control signals to the EM power source 12 to control the power output to the applicators to maintain the temperature substantially constant for the selected treatment time period. This time period is set by timer 46, and will usually be about an hour. At the end of the treatment time, the oscillator is automatically turned off by timer 46. However, the power can be turned off at any time using the "off" switch 30.

Figure 7:
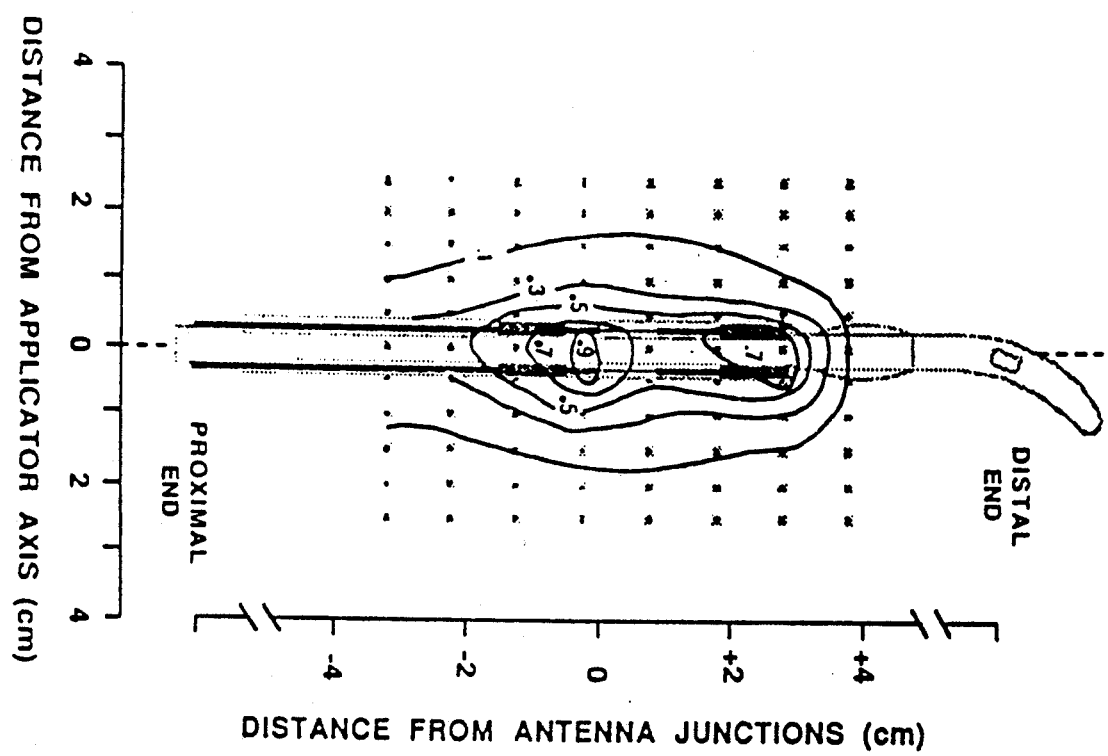
FIG. 7 is a diagram showing the energy specific adsorption rate (SAR) distribution of microwave energy transmitted from energy applicators positioned in the apparatus when positioned in the prostate.

The apparatus was tested using muscle equivalent phantom material having a relative dielectric = 69.0 and conductivity = 1.4 mho/m to simulate prostate tissues at a frequency of 630 MHz and the Iso-SAR (specific-absorption-rate) distribution of applicator curves is charted as shown in FIG. 7. FIG. 7 shows the adsorption rate curves in a plane substantially tangential to the perimeter of the inserter apparatus 18. The test parameters were as follows:

Frequency = 630 MHz
SAR at 100% = 478 W/kg at a 1.0 value
Forward power = 21 Watts (divider input)
Reflected power = 1 Watts As shown in FIG. 7, the measurement boundaries were 5 cm in the horizontal direction and 7 cm in the length direction. The SAR gradient was 478 W/kg at the hottest point which was used to normalize the curves at 0.1, 0.3, 0.5, 0.7, and 0.9 representing respectively 10%, 30%, 50%, 70%, and 90% of the maximum value. The rate of the initial temperature rise is proportional with these SAR percentages. Thus, the tested applicator array provides the long, uniform, shallow heat pattern desired for treating diseased tissue enlargement around and along the urethral passage through the prostate gland.

Figure 10:
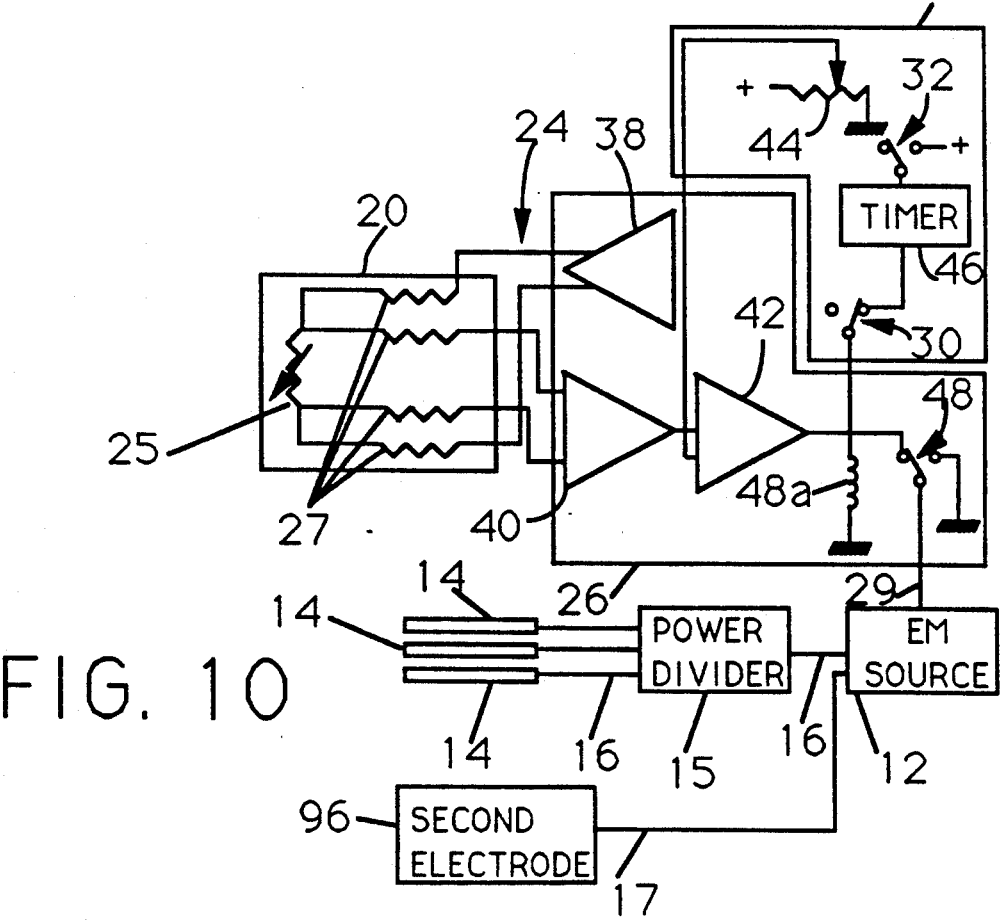
FIG. 10 is view similar to that of FIG. 2 but showing the system of FIG. 9.
Figure 9:
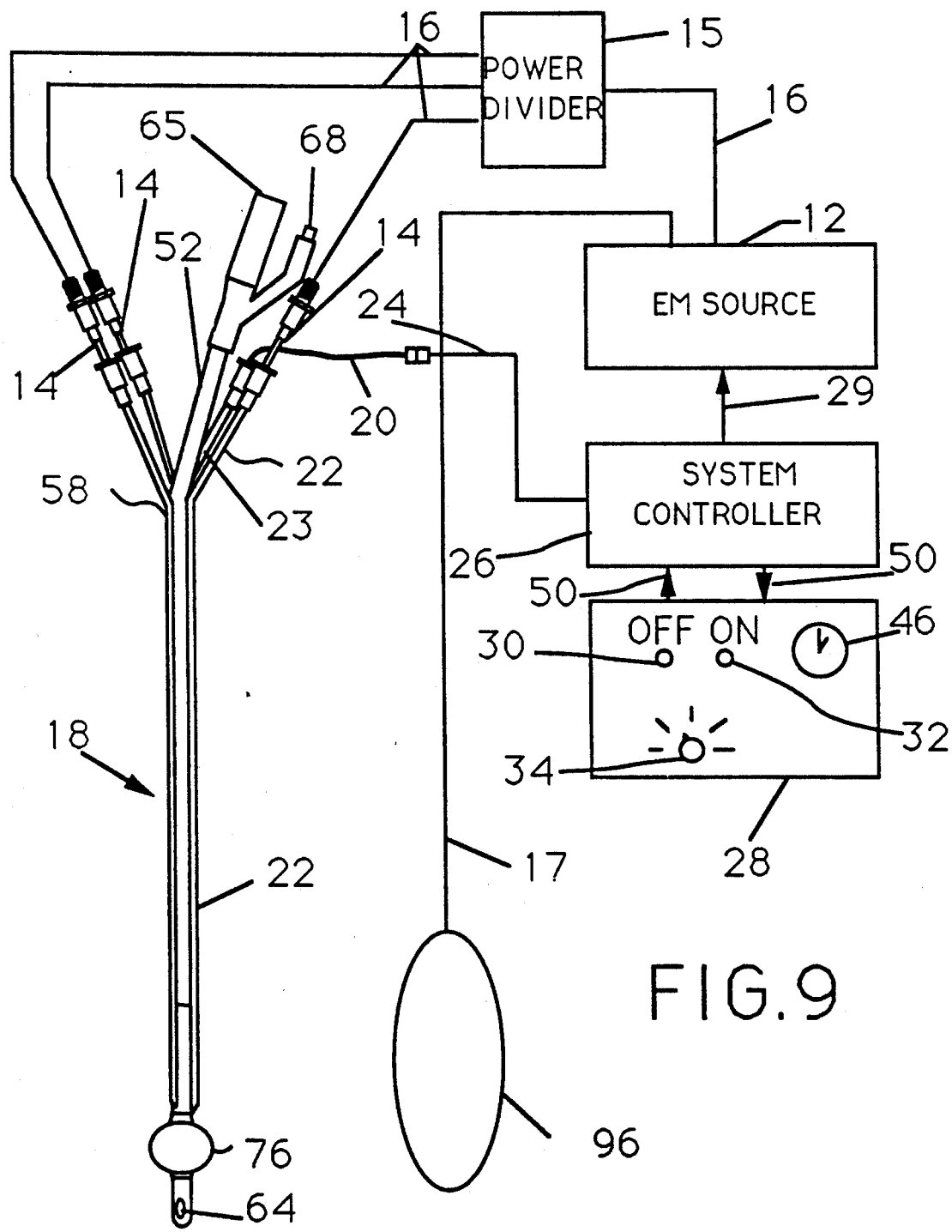
FIG. 9 is a view similar to that of FIG. 1 showing an embodiment of the system usable with below microwave frequency power and including an additional electrode.

FIG. 9 shows a system block diagram similar to FIG. 1 except that an additional second metallic electrode 96, such as a large surface contacting metal plate or insertable metal cylinder, is shown connected by a second coaxial cable 17 to the EM source 12. This embodiment is an alternate embodiment for use with below microwave frequencies. With this embodiment, EM source 12 is adapted to generate opposing phase polarity outputs. The signal sent to applicators 14 is of a common polarity while the opposing polarity signal is connected to electrode 96. Electrode 96 provides a current flow path for current to flow away from applicators 14 into the tissue. Electrode 96 may be applied either in contact or near contact with the lower anterior pelvic surface of the patient being treated, or it may be inserted, when in cylindrical shape, into the rectal passage adjacent to the prostate gland. As the current flows from the applicators 14 toward the electrode 96 which is much larger in tissue contacting surface area than the applicators 14, the current and heating is reduced. Therefore the primary heating is limited to the region surrounding applicators 14, i.e., the urethral passage through the prostate. FIG. 10 shows details of the control system for the embodiment of FIG. 9, and is similar to FIG. 2, except for the showing of the additional electrode 96 connected to the EM source 12 by cable 17. As explained above, EM source 12 provides outputs of opposing phase to applicators 14 and additional electrode 96.

Figure 11:
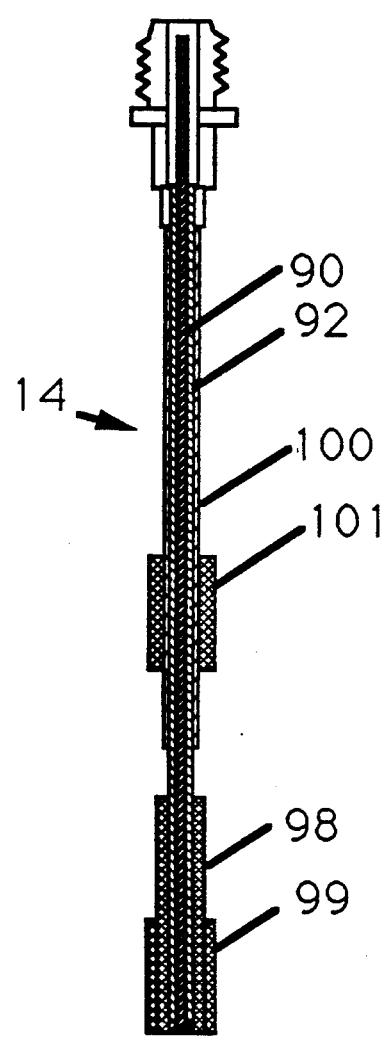
FIG. 11 is a longitudinal section of a urethral insertable EMR microwave applicator.

FIG. 11 shows, in longitudial section, a preferred embodiment of a urethral insertable EMR microwave applicator 14 for operation at microwave frequencies. A similar applicator was used in the clinical pilot study described herein. The applicator 14 is constructed from a length of flexible coaxial cable with center conductor 90 and surrounding dielectric section 92 extending beyond the outer conductor 100. A metallic cylinder 98 is attached to the end of center conductor 90, with an additional cylinder 99 mounted thereon. A third cylinder 101 is electrically attached to outer conductor 100. The heating zone of the applicator is between the applicator tip and cylinder 101. This distance will usually be about 5 cm for use in the prostate. The use of additional cylinders 99 and 101 provide a fairly uniform heat distribution over the heating zone of the applicator.

Figure 12:
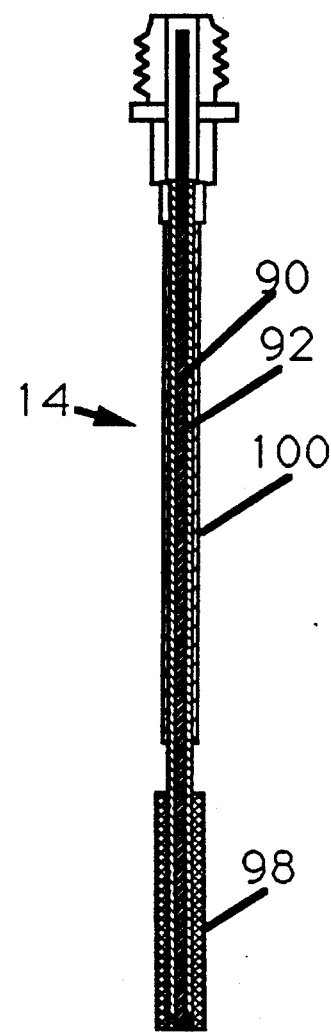
FIG. 12 is a longitudinal section of a urethral insertable EMR capacitive electrode or applicator.

FIG. 12 shows, in longitudinal section, a preferred embodiment of a urethral insertable EMR capacitive electrode applicator for operation at below microwave frequencies. Again, the applicator 14 is constructed from a length of flexible coaxial cable. The center conductor 90 and dielectric section 92 are extended beyond the outer conductor 100. A metallic cylinder 98 is attached to the end of the center conductor 90. For electrode style applicators, which are operated below microwave frequencies, it is preferred that the capacitance to the tissue from the active electrode portion, here metallic cylinder 98, be larger than the capacitance for the same length section of the inserted connecting cable to the active electrode region. In this way the heating will be more intense in the tissue surrounding the active portion of the electrode intended to be heated than around the inserted interconnecting electrode cable. At below microwave frequencies, with the applicator of FIG. 12, the heating occurs over the length of the cylinder 98. The applicator of FIG. 12 can also operate as a microwave applicator.

For use in the apparatus of the invention, it has been found that cylinders 98, 99 and 101 of the applicators may be rigid if kept to less than about 3 cm in length. If rigid, the cylinders may be made of copper. Various constructions of cylinder 98 which are flexible are shown in FIGS. 13-18.

Figure 13:
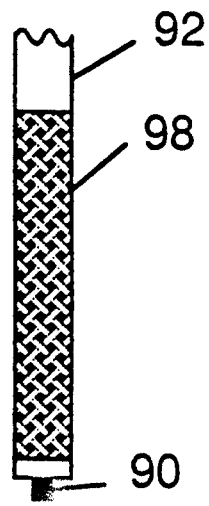
FIG. 13 is a fragmentary elevational view of a flexible, multiple were coil configuration for an applicator of the invention.

FIG. 13 shows cylinder 98 comprised of multiple over lapping strands of wire forming an inter-twined or inter-woven braid cylinder. The cylinder is electrically connected to the center conductor 90 of the applicator for use with either below microwave or microwave frequencies.

Figure 14:
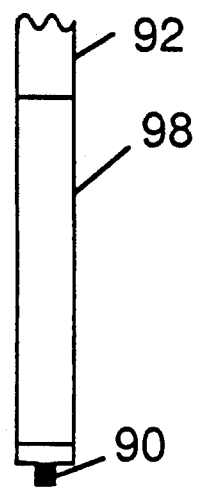
FIG. 14 is a fragmentary elevational view of a flexible conductive rubber or metallic plated applicator of the invention.

FIG. 14 shows cylinder 98 comprised of a conductive rubber or plated dielectric surface. This type of material is commercially available and provides an alternate method of constructing the flexible electrode surface. The cylinder is electrically connected to the center conductor 90 of the applicator for use with either below microwave or microwave frequencies.

Figure 15:
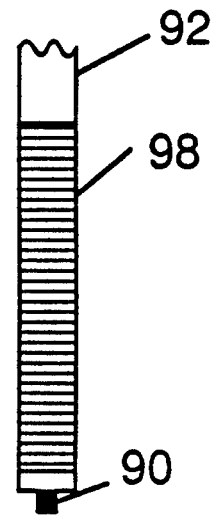
FIG. 15 is a fragmentary elevational view of a helical coil wire wrap configuration for an applicator of the invention.

FIG. 15 shows cylinder 98 comprised of a single helical coil wire wrap configuration. The cylinder is electrically connected to the center conductor 90 of the applicator for use with below microwave frequencies where the applicator operates as a capacitive electrode. At microwave frequencies, the coil could be connected to either the center conductor 90, the outer conductor 100, or both the center and outer conductors at opposing ends of the cylinder.

Figure 16:
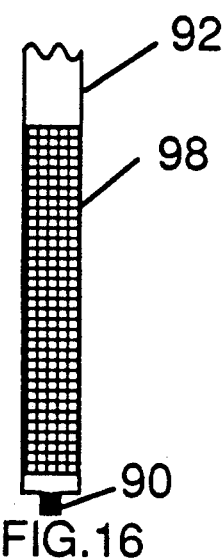
FIG. 16 is a fragmentary elevational view of a wire mesh or screen configuration for an applicator of the invention.

FIG. 16 shows cylinder 98 comprised of a wire grid, mesh, or screen. The cylinder is electrically connected to the center conductor 90 of the applicator for below microwave frequencies where the applicator operates as a capacitive electrode. At microwave frequencies, the wire structure could be connected to either the center conductor 90, the outer conductor 100, or both at opposing ends of the wire structure.

Figure 17:
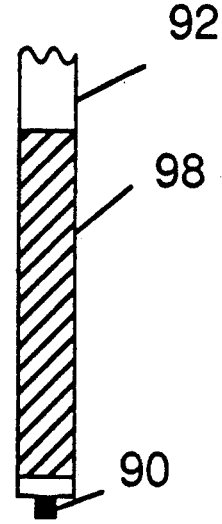
FIG. 17 is a fragmentary elevational view of a multiple wire coil wrap configuration for an applicator of the invention.

FIG. 17 shows cylinder 98 comprised of several non-overlapping wires which are wound in parallel coils along the same length section. The cylinder is electrically connected to the center conductor 90 of the applicator for below microwave frequencies where the applicator operates as a capacitive electrode. At microwave frequencies, the coils could be connected to either the center conductor 90, the outer conductor 100, or both at opposing ends of the coil.

Figure 18:
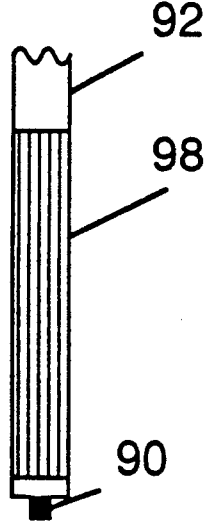
FIG. 18 is a fragmentary view of a multiple flexible wire configuration for an applicator of the invention.

FIG. 18 shows cylinder 98 comprised of one or more parallel wires which run the full length of the active heating length. The cylinder is electrically connected to the center conductor of the applicator for below microwave frequencies where the applicator operates as a capacitive electrode. At microwave frequencies, the cylinder could be connected to either the center conductor 90, the outer conductor 100, or to both conductors at opposing ends of the wires.

Figure 19:
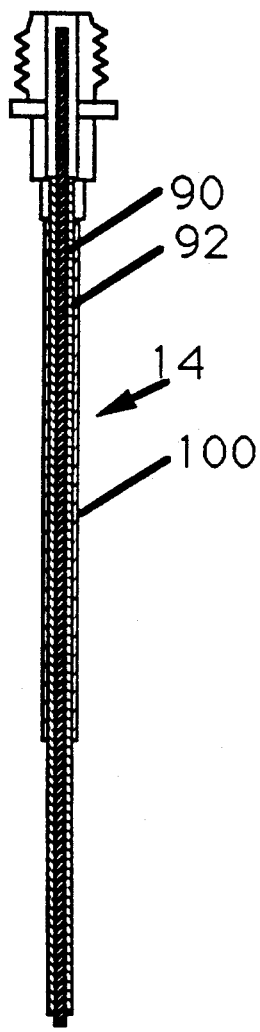
FIG. 19 is a longitudial section of a basic applicator usable with the invention.

FIG. 19 shows the active heating area of the applicator 14 as being comprised of the center conductor 90 and dielectric cylinder 92 of the coaxial cable which has been exposed by the removal of the outer conductor 100 in the tip region of the coaxial conductor cable. This form of applicator would operate for the below microwave frequencies, where the applicator operates as a capacitive electrode, and at microwave frequencies, where the center conductor wire 90 acts as a microwave antenna radiator.

It is preferred for the various applicators described that they be relatively snugly received within the applicator tubes to provide good EMR energy transfer to the tissue to be heated. Similarly, the temperature sensor should be relatively snugly received in the temperature sensor tube. However, the tubes are sized so that the applicator and temperature sensor can be inserted and withdrawn therefrom.

RESULTS OF PILOT CLINICAL TRIAL

Figure 8:
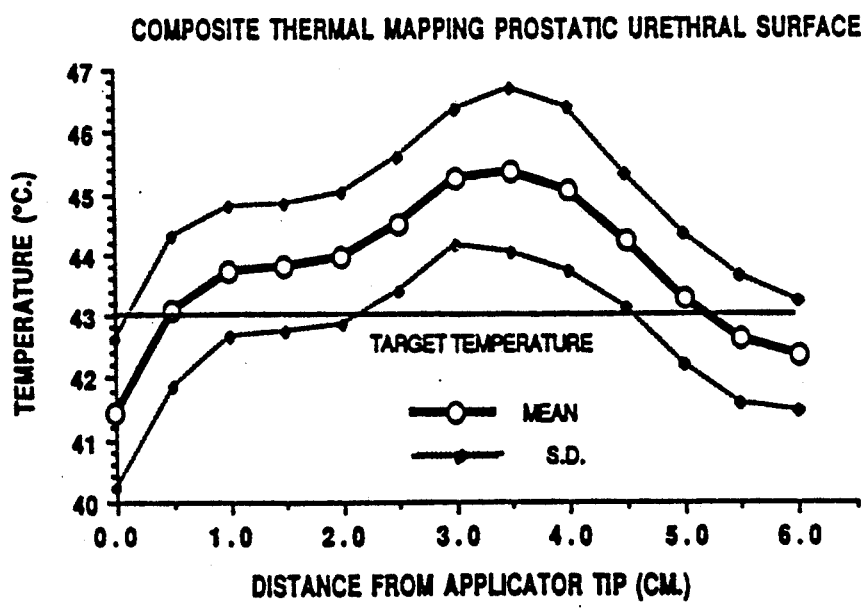
FIG. 8 is a composite plot of statistically compiled clinically observed temperature within patients treated during a pilot study vs. the position of the temperature sensor along the prostatic urethral surface measured by the thermal mapping temperature track.

A pilot clinical trial was conducted from March 1987 to July 1988, treating 21 men, at Norris Cancer Center under the direction of M. Sapozink, M.D., Ph.D., S. Boyd, M.D., M. Astrahan, Ph.D., G. Jozsef, Ph.D., S. Nourparvar, B.S., and Z. Petrovich, M.D. The results of this study were first reported at the North American Hyperthermia Group Meeting on Mar. 18, 1989. The patients in this study had a mean age of 67 years, a mean Karnofsky performance staus of 93%, and mean prostate volume of 91 cc. The eligibility for protocol entry included the severity of the symptomatology such that a transurethral resection of the prostate (TURP) had been suggested (100%) (although there were two patients that were considered medically inoperable because of chronic anticoagulation). The patient's symptoms included for all patients urination frequency, nocturia, symmetric homgeneous enlargement on digital and CT examination, normal prostatic acid phosphatase and prostate specific antigen, negative cystoscopy, post void residual urine volume greater than 100 cc (86%), decreased urinary stream with urine flow rate under 15 cc/second, and prostate biopsy demonstrating hyperplasia without evidence of malignancy. Other patient symptoms included urinary dribbling, recurrent urinary tract infections, and impotence. One of the 21 patients had received a prior TURP. The coaxial microwave applicator design used in this study was similar to that shown in FIG. 11, and to the applicators shown in Turner U.S. Pat. No. 4,669,475. Three of these coaxial microwave antennae were used equally spaced around the perimeter of a modified Foley balloon urinary catheter as described above and illustrated in the drawings. The tubes 22 in which the antennae were inserted were 16 gauge closed tipped catheters, as was tube 23 for the temperature sensor. These catheters were attached to the outer wall of the Foley catheter with silicone rubber adhesive. The operating frequency for these antennae was either 630 or 915 MHz depending on the hyperthermia system. The antennae design additionally included a temperature sensor in each of the coaxial antennae, it being placed in the center of the heating length of the antenna. The temperature distribution along the inserted antenna/catheter assembly was determined by manually repositioning the additional temperature sensor corresponding to temperature sensor 20 in the drawings, at various positions along the catheter length while the microwave power was being controlled by one of the temperature sensors inside the coaxial antenna. This process is called thermal mapping. The heating pattern created by this array has been observed to be ellipsoidal with the long axis of the ellipse lying along the catheter length. There were 177 treatment sessions given either once or twice per week. FIG. 8 shows a composite of the temperature distribution observed with the thermal mapping temperature sensor for these treatments. Note that the distance measurement was from the tip of the inserted antenna applicator. This allowed the temperature, from each treatment at a common position from the tip, to be statistically averaged with all other treatments for that same distance from the tip to obtain the mean temperature and the standard deviation. It can be seen that the mean temperature exceeded 43 degrees Celsius for about 4.5 cm of the length starting at about 0.5 cm from the antenna tip. This length corresponds well with the typical 5 cm diameter of an enlarged prostate gland. In 173 of the 177 treatment sessions a temperature of greater than 42 degrees Celsius was achieved at some point along the urethral surface as measured by the thermal mapping temperature sensor. Acute toxicity was common but relatively minor as shown in the following table 1:

TABLE 1

| Acute Toxicity & Complications (Mean Follow-up-10 Months-All Were Treatment Related) | | |
|---|---|---|
| Acute Toxicity | % of Sessions | % of Patients |
|  | 177 Total | 21 Total |
| Bladder Spasm | 26 | 71 |
| Hematuria | 23 | 71 |
| Dysuria | 9 | 48 |
| Urethal Pain* | 8 | 43 |
| Complications | 0 | 0 |

*Power limiting in one patient

The urethral pain was only power limiting in one patient who had a urethral stricture. The bladder spasms were primarily noted during the hyperthermia session, however, they would occasionally occur in the period of time between treatment sessions and result in transient stress incontinence. These acute toxicities are considered very mild compared to the trauma resulting from the common surgical treatment procedure (TURP).

These 21 patients were evaluated for the response to treatment with both subjective and objective parameters. The objective parameters which could be measured were prostate volume, residual urine volume retained in the bladder, and the urine flow rate. The subjective parameters measured were daytime urination frequency, nocturnal or night time frequency of urination, and urine stream force. Table 2 shows the results of the objective parameters and Table 3 shows the results of the subjective parameters.

TABLE 2

| Results-Objective Parameters | | | |
|---|---|---|---|
|  | Baseline | Follow-Up | p-Value (paired t-test) |
| Prostate Volume (cc) | 91 | 86 | 0.40 |
| Residual Urine Volume (cc) | 177 | 91 | 0.001 |
| Urine Flow Rate (cc./sec.) | 11.0 | 15.9 | <0.001 |

The objective parameters all showed improvement. Significant improvement was observed in both the reduction of the retained urine in the bladder following voiding and the urine flow rate. This is shown by the statistical p-value or probability of correlation between the treatment and the improvement of the condition. The condition of retained urine contributes to infections and other patient problems.

TABLE 3

| Results-Subjective Parameters | | | |
|---|---|---|---|
|  | Baseline | Follow-up | P-Value (paired t-test) |
| Daytime Freq. (Every X hours) | 2.4 | 2.8 | 0.24 |
| Nocturnal Freq. (X per night) | 3.7 | 2.2 | <0.001 |
| Stream Force | 1.3 | 1.7 | 0.002 |

The assessment of stream force was from 0, meaning total retention, to 3, meaning strong flow. Improvement was seen from the pretreatment baseline condition to the follow-up condition. Every parameter of the subjective results was also shown to improve. There was a 10 month mean follow-up for these patients. Only two of these patients have required TURP for persistent or recurrent symptoms. One of these had been in complete retention condition at the time of treatment.

As a summary of the pilot clinical study it was determined that transurethral microwave hyperthermia is feasible. Intracavitary periurethral temperatures from 42-47 degrees Celsius were routinely obtained in these patients. Treatment associated morbidity was frequent, but mild, required little intervention, and was power limiting in only one case. The post-treatment complication rate was 0%. Significant improvements in nocturnal urinary frequency, stream force, post voiding residual urine volume, and urine flow rates were observed.

Whereas this invention is here illustrated and described with specific reference to an embodiment thereof presently contemplated as the best mode of carrying out such invention in actual practice, it is to be understood that various changes may be made in adapting the invention to different embodiments without departing from the broader inventive concepts disclosed herein and comprehended by the claims that follow.

We claim:

1. Apparatus for removably holding and positioning a plurality of electromagnetic energy applicators in a urethral passage extending through a prostate gland, comprising:

a flexible urinary catheter having substantially tubular shape and an insertion end for insertion through the urethral passage and bladder neck into the bladder, said catheter providing a fluid drainage means to remove fluid filling the bladder;

balloon means mounted on the urinary catheter near the insertion end and adapted to be inserted into the bladder with the insertion end of the urinary catheter;

means for inflating the balloon means after insertion of the balloon means into the bladder, whereby the inflated balloon means will seat in the bladder neck to thereby hold the inserted urinary catheter in fixed position in the urethral passage;

a plurality of applicator receiving passages each sized to removably receive an electromagnetic energy applicator therein, said applicator receiving passages extending along the length of the urinary catheter a predetermined distance toward the insertion end thereof so that with the insertion end of the urinary catheter in the bladder, the balloon means inflated, and the urinary catheter fixed in place in the bladder, said applicator receiving passages extend substantially through the prostate gland whereby an electromagnetic energy applicator inserted into an applicator receiving passage can be positioned in the applicator receiving passage within the prostate gland so that electromagnetic energy applied by the applicator will cause heating of the prostate tissue surrounding the applicator; and a plurality of electromagnetic energy applicators, an applicator of the plurality of applicators being removably received within each of the applicator receiving passages.

2. Apparatus according to claim 1, wherein a plurality of applicator receiving passages are provided uniformly spaced about the perimeter of the urinary catheter.

3. Apparatus according to claim 2, wherein there are three applicator receiving passages.

4. Apparatus according to claim 1, wherein the applicator receiving passages are formed by applicator tubes secured to the urinary catheter by gluing.

5. Apparatus according to claim 4, wherein the applicator tubes are secured to the urinary catheter by a silicone rubber adhesive.

6. Apparatus according to claim 1, additionally including a temperature sensor receiving passage sized to receive a temperature sensor therein, said temperature sensor receiving passage extending along the length of the urinary catheter a predetermined distance toward the insertion end thereof so that with the insertion end of the urinary catheter in the bladder, the balloon means inflated, and the urinary catheter fixed in place in the bladder, said temperature sensor receiving passage extends through a desired portion of the prostate gland whereby a temperature sensor inserted into the temperature sensor receiving passage can be positioned in the temperature sensor receiving passage within the prostate gland so that the temperature of the prostate tissue surrounding the urethral passage through the desired portion of the prostate gland can be measured.

7. Apparatus according to claim 6, wherein the temperature sensor receiving passage is formed by a temperature sensor tube secured to the urinary catheter by gluing.

8. Apparatus according to claim 1, wherein the inserted electromagnetic energy applicators are microwave antennae.

9. Apparatus according to claim 1, wherein the inserted electromagnetic energy applicators operate as capacitive electrodes when electromagnetic energy below microwave frequencies is applied by said applicators.

10. Apparatus according to claim 9, wherein the plurality of applicator receiving passages are provided around the perimeter of the urinary catheter and each of the inserted electromagnetic energy applicators apply electromagnetic energy of a differing phase so that heating currents will pass through the prostate tissue between the applicators.

11. Apparatus according to claim 10, additionally including an electromagnetic energy generator, said electromagnetic energy generator including a source of electromagnetic energy and a phase transforming power divider means connected between the source of electromagnetic energy and the inserted electromagnetic energy applicators, wherein the phase transforming power divider means provides power of differing phase to each of the inserted applicators, and wherein the differing phase provided by said phase transforming power divider means is defined as 360 degrees divided by the number of inserted applicators.

12. Apparatus according to claim 9, additionally including an electromagnetic energy generator which generates signals of opposing phase, means connecting the inserted electromagnetic energy applicators to the electromagnetic energy generator to provide electromagnetic energy of common phase to the inserted electromagnetic energy applicators, an additional electrode, and means connecting the additional electrode to the electromagnetic energy generator to provide electromagnetic energy of opposing phase to the additional electrode so that heating currents will pass through the prostate tissue between the inserted applicators and the additional electrode.

13. A system for heating the prostate gland, comprising:

a flexible urinary catheter having substantially tubular shape and an insertion end for insertion through the urethral passage and bladder neck into the bladder, said catheter providing a fluid drainage means to remove fluid filling the bladder;

balloon means mounted on the urinary catheter near the insertion end and adapted to be inserted into the bladder with the insertion end of the urinary catheter;

means for inflating the balloon means after insertion of the balloon means into the bladder, whereby the inflated balloon means will seat in the bladder neck to thereby hold the inserted urinary catheter in fixed position in the urethral passage;

a plurality of applicator receiving passages each sized to removably receive an electromagnetic energy applicator therein, said applicator receiving passages extending along the length of the urinary catheter a predetermined distance toward the insertion end thereof so that with the insertion end of the urinary catheter in the bladder, the balloon means inflated, and the urinary catheter fixed in place in the bladder, said applicator receiving passages extend substantially through the prostate gland whereby an electromagnetic energy applicator inserted into an applicator receiving passage can be positioned in the applicator receiving passage within the prostate gland so that electromagnetic energy applied by the applicator will cause heating of the prostate tissue surrounding the applicator;

a plurality of electromagnetic energy applicators, an electromagnetic energy applicator of the plurality of electromagnetic energy applicators being inserted into each of the respective applicator receiving passages of the plurality of applicator receiving passages;

an electromagnetic energy generator operatively coupled to the plurality of electromagnetic energy applicators for supplying electromagnetic energy to the applicators;

temperature sensor means for sensing the temperature of a selected portion of the prostate gland during heating and producing output signals representative of the temperature sensed;

temperature setting means for providing a reference signal representative of the desired temperature to which the prostate gland is to be heated; and control means for comparing the signal representative of the temperature sensed and the reference signal and providing a control signal to the electromagnetic energy generator to control the electromagnetic energy supplied by the generator to the applicators to maintain the temperature of the prostate tissue surrounding the applicators substantially at the desired temperature.

14. A system according to claim 13, wherein the inserted electromagnetic energy applicators are microwave radiating antennae.

15. A system according to claim 14, wherein the microwave antennae are microwave interstitial coaxial cable applicators.

16. A system according to claim 13, wherein the plurality of applicator receiving passages are provided around the perimeter of the urinary catheter, wherein an applicator is inserted into each of the applicator receiving passages, wherein the inserted applicators operate as capacitive electrodes, and wherein the electromagnetic energy generator supplies electromagnetic energy of below microwave frequencies and of differing phase to each of said applicators so that heating current will pass through the prostate tissue between the applicators.

17. A system according to claim 16, wherein the electromagnetic energy generator includes a phase transforming power divider means for providing power of differing phase to each of the inserted applicators and wherein the differing phase provided to each applicator is defined as 360 degrees divided by the number of inserted applicators.

18. A system according to claim 16, wherein the inserted electrode applicators have a heating portion and a non-heating interconnecting portion, and wherein the heating portion has increased capacitance to tissue adjacent thereto compared to the interconnecting portion.

19. A system according to claim 13, wherein the inserted electromagnetic energy applicators operate as capacitive electrodes, wherein the system includes an additional electrode operatively coupled to the electromagnetic energy generator and adapted to be spaced from the inserted applicators and operatively coupled to the body in which the prostate to be heated is located, and wherein the electromagnetic energy generator provides electromagnetic energy of one phase to the inserted applicators and electromagnetic energy of differing phase to the additional electrode so that heating currents will pass between the inserted applicators and the additional electrode.

20. A system according to claim 19, wherein the inserted electrode applicators have a heating portion and a non-heating, interconnecting portion, and wherein the heating portion has increased capacitance to the tissue adjacent thereto compared to the interconnecting portion.

21. A system according to claim 19, wherein the additional electrode has a larger surface contact area than the inserted applicators, and wherein the additional electrode is adapted to be placed in contact with a portion of the outer skin surface of the body.

22. A system according to claim 19, wherein the additional electrode has a larger surface contact area than the inserted applicators, and wherein the additional electrode is adapted to be placed in the rectal passage adjacent to the prostate gland region.

23. A system according to claim 19, wherein the additional electrode has a larger surface contact area than the inserted applicators, and wherein the additional electrode is adapted to be capacitively coupled to a portion of the outer skin surface of the body.

24. A system for heating the prostate gland, comprising:

a flexible urinary catheter having substantially tubular shape and an insertion end for insertion through the urethral passage and bladder neck into the bladder, said catheter providing a fluid drainage means to remove fluid filling the bladder;

balloon means mounted on the urinary catheter near the insertion end and adapted to be inserted into the bladder with the insertion end of the urinary catheter;

means for inflating the balloon means after insertion of the balloon means into the bladder, whereby the inflated balloon means will seat in the bladder neck to thereby hold the inserted urinary catheter in fixed position in the urethral passage;

at least one applicator receiving passage sized to receive an electromagnetic energy applicator therein, said at least one applicator receiving passage extending along the length of the urinary catheter a predetermined distance toward the insertion end thereof so that with the insertion end of the urinary catheter in the bladder, the balloon means inflated, and the urinary catheter fixed in place in the bladder, said at least one applicator receiving passage extends substantially through the prostate gland whereby an electromagnetic energy applicator inserted into the applicator receiving passage can be positioned in the applicator receiving passage within the prostate gland so that electromagnetic energy applied by the applicator will cause heating of the prostate tissue surrounding the applicator;

at least one electromagnetic energy applicator inserted into the at least one applicator receiving passage;

an electromagnetic energy generator operatively coupled to the at least one electromagnetic energy applicator for supplying electromagnetic energy to the at least one applicator;

temperature sensor means for sensing the temperature of the prostate gland during heating and producing output signals representative of the temperature sensed;

temperature setting means for providing a reference signal representative of the desired temperature to which the prostate gland is to be heated; and control means for comparing the signal representative of the temperature sensed and the reference signal and providing a control signal to the electromagnetic energy generator to control the electromagnetic energy supplied by the generator to the at least one applicator to maintain the temperature of the prostate tissue surrounding the at least one applicator substantially at the desired temperature.

* * * * *